United States Patent
Lee

(10) Patent No.: US 10,436,716 B2
(45) Date of Patent: Oct. 8, 2019

(54) UBIQUITOUS TRANSMISSIVE RAMAN SPECTROSCOPY FOR STAND-OFF DETECTION

(71) Applicant: Smiths Detection, Inc., Edgewood, MD (US)

(72) Inventor: Vincent Yuan-Hsiang Lee, Winchester, MA (US)

(73) Assignee: Smiths Detection, Inc., Edgewood, MD (US)

( * ) Notice: Subject to any disclaimer, the term of this patent is extended or adjusted under 35 U.S.C. 154(b) by 30 days.

(21) Appl. No.: 14/495,295

(22) Filed: Sep. 24, 2014

(65) Prior Publication Data

US 2016/0084765 A1    Mar. 24, 2016

(51) Int. Cl.
*G01N 21/65* (2006.01)
*G01J 3/44* (2006.01)
*G01J 3/02* (2006.01)

(52) U.S. Cl.
CPC ............ *G01N 21/65* (2013.01); *G01J 3/0291* (2013.01); *G01J 3/44* (2013.01)

(58) Field of Classification Search
CPC ........... G01N 21/65; G01N 2021/0342; G01N 2021/052; G01N 2021/651; G01N 2021/653; G01N 2021/655; G01N 2021/95615; G01N 2033/0081; G01N 21/0303; G01N 21/3563; G01N 21/3581; G01N 21/47; G01N 21/64; G01N 21/9018; G01N 33/22; G01N 33/442; B07C 5/34; G01J 3/44; Y10T 156/10; Y10T 436/143333; Y10T 436/24
See application file for complete search history.

(56) References Cited

U.S. PATENT DOCUMENTS

| | | | | |
|---|---|---|---|---|
| 5,139,025 A * | 8/1992 | Lewis | ................... | A61B 5/0091 600/475 |
| 5,459,313 A * | 10/1995 | Schrader | ............ | G01N 21/9018 209/524 |
| 5,534,997 A * | 7/1996 | Schrader | ................ | G01N 21/65 356/301 |
| 5,935,062 A * | 8/1999 | Messerschmidt | .. | G01N 21/4738 600/322 |
| 6,310,686 B1 * | 10/2001 | Jiang | ......................... | G01J 3/02 356/301 |
| 6,313,423 B1 * | 11/2001 | Sommer | ................. | B07C 5/342 209/577 |
| 6,753,966 B2 * | 6/2004 | Von Rosenberg | ........ | G01J 3/02 356/432 |

(Continued)

OTHER PUBLICATIONS https://www.rp-photonics.com/beam_waist.html.*

(Continued)

*Primary Examiner* — Mohamed K Amara
(74) *Attorney, Agent, or Firm* — Kevin E. West; Advent, LLP

(57) ABSTRACT

A substance analysis system and method are provided, the system disposable a variable stand-off distance from a substance in situ, including an emitter disposed to emit radiation onto the substance in situ, and a detector disposed the variable stand-off distance from the substance in situ, the detector comprising a receiver defining a substantially collimated collection path over the variable stand-off distance.

31 Claims, 5 Drawing Sheets

(56) References Cited

U.S. PATENT DOCUMENTS

| | | | | |
|---|---|---|---|---|
| 6,809,812 | B2* | 10/2004 | Yin | G01J 3/02 356/301 |
| 6,826,422 | B1* | 11/2004 | Modell | A61B 1/00059 250/461.2 |
| 6,847,490 | B1* | 1/2005 | Nordstrom | A61B 1/00062 359/642 |
| 6,862,091 | B2* | 3/2005 | Johnson | G01J 3/02 356/319 |
| 7,652,763 | B2* | 1/2010 | Matousek | A61B 5/0059 356/301 |
| 7,889,348 | B2* | 2/2011 | Tearney | A61B 1/043 356/451 |
| 7,911,604 | B2* | 3/2011 | Matousek | A61B 5/417 356/301 |
| 8,115,934 | B2* | 2/2012 | Boppart | A61B 5/0066 356/479 |
| 2002/0049389 | A1* | 4/2002 | Abreu | A61B 3/1241 600/558 |
| 2002/0190198 | A1 | 12/2002 | Mickael | |
| 2003/0220549 | A1* | 11/2003 | Liu | A61B 5/0059 600/317 |
| 2004/0054270 | A1* | 3/2004 | Pewzner | A61B 5/14546 600/341 |
| 2004/0063214 | A1* | 4/2004 | Berlin | G01N 21/65 436/94 |
| 2004/0263843 | A1* | 12/2004 | Knopp | G01J 3/44 356/301 |
| 2005/0127285 | A1* | 6/2005 | Kampf | G01N 33/442 250/281 |
| 2005/0283058 | A1* | 12/2005 | Choo-Smith | A61B 5/0066 600/315 |
| 2008/0062429 | A1* | 3/2008 | Liang | A61B 1/00039 356/497 |
| 2008/0177139 | A1* | 7/2008 | Courtney | A61B 5/0062 600/109 |
| 2009/0141271 | A1* | 6/2009 | Matousek | A61B 5/417 356/301 |
| 2009/0177052 | A1* | 7/2009 | Rebec | A61B 5/14532 600/310 |
| 2009/0248322 | A1* | 10/2009 | Hlavaty | G01N 21/3563 702/28 |
| 2010/0053606 | A1* | 3/2010 | Matousek | G01N 21/65 356/301 |
| 2012/0133933 | A1* | 5/2012 | Zou | G01N 21/0303 356/301 |
| 2014/0060189 | A1* | 3/2014 | Sausa | G01N 21/3563 73/579 |
| 2014/0104611 | A1* | 4/2014 | Watson | G01J 3/06 356/326 |
| 2014/0252234 | A1* | 9/2014 | Lee | G01N 21/65 250/341.1 |
| 2016/0327779 | A1* | 11/2016 | Hillman | G02B 21/367 |
| 2017/0234728 | A1* | 8/2017 | Buller | G02B 26/101 356/402 |

OTHER PUBLICATIONS

Sanchita Sil & Siva Umapathy; Raman spectroscopy explores molecular structural signatures of hidden materials in depth: Universal Multiple Angle Raman Spectroscopy; Scientific Reports; 2014; pp. 1-7; 4, 5308

Internaternational Search Report and Written Opinion dated Jan. 5, 2016 for PCT/US2015/051823.

International Preliminary Report on Patentability dated Mar. 28, 2017 for PCT/US2015/051823.

* cited by examiner

UBIQUITOUS TRANSMISSIVE RAMAN SPECTROSCOPY FOR STAND-OFF DETECTION

BACKGROUND

The present disclosure relates to spectroscopy, and more particularly to transmission Raman spectroscopy. There may be situations in which a substance is encountered, the components of which are unknown. It may not be immediately obvious what components are present in the substance. For example, one might not be able to tell what components a substance contains by simply looking at the substance. Moreover, it might not be immediately obvious whether the substance contains impurities, illicit and/or dangerous components, ingredients of interest, or the like. Thus, it may be convenient or advisable for an investigator to stand off a variable or safe distance from such a substance while performing in situ analysis.

SUMMARY

A substance analysis system disposable a variable stand-off distance from a substance in situ and methods are described that employ a detector with a collection aperture. In an implementation, the substance analysis system that employs the techniques of the present disclosure includes an emitter disposed to emit radiation into the substance and cause reflected radiation within the substance and a detector disposed the variable stand-off distance from the substance in situ, the detector comprising a receiver defining a substantially collimated collection path over the variable stand-off distance, the receiver configured to receive a transmission Raman signal from a substantially collimated portion of the substance.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

Exemplary embodiments are described with reference to the accompanying figures. In the figures, the left-most digit(s) of a reference number may identify the figure in which the reference number first appears. The use of the same reference number in different instances in the description and the figures may indicate similar or identical items.

DETAILED DESCRIPTION

Determining the components of substances may be useful in many situations. For example, it may be useful to prevent substances containing illicit and/or dangerous components from being transported, such as by airplane passengers carrying fluids, pastes, powders, or the like, that may need to be checked to determine whether the substances contain any illicit, dangerous, or other components of interest. In another example, it may be useful to analyze substances to determine whether they contain impurities, for substances flowing through containers such as conduits, substances stored in containers such as packaging, or the like. In many scenarios, however, analysis of substances is further complicated by the fact that the substances are located in containers, such as in the cases of airplane passengers carrying bottles, for example, or where factories may have substances of interest flowing through piping, or where medicine makers may store medicine in containers, or the like. Some users may want to analyze a substance without having to remove the substance from its container, such as by non-invasive substance analysis, regardless of whether the container is substantially transparent, translucent, or substantially opaque, and regardless of whether the substance is approachable, movable or removable.

Figure 1:
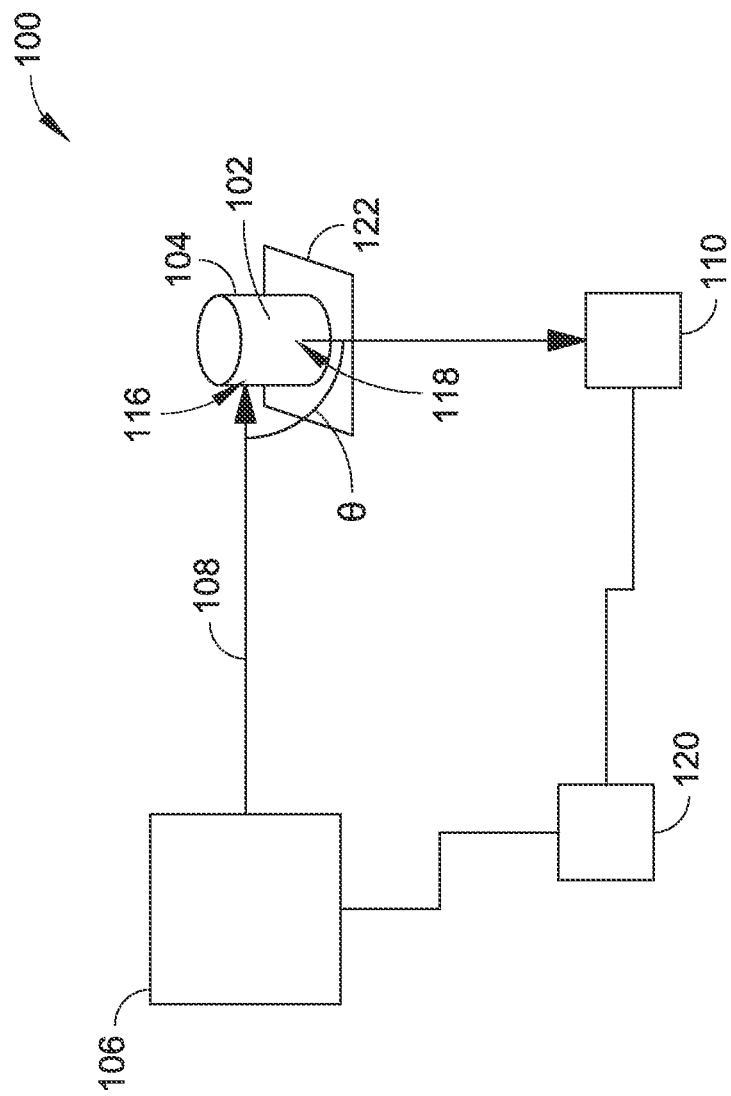
FIG. 1 is a schematic illustration of an exemplary system embodiment configured to analyze a substance from a stand-off distance, without moving or touching the substance, based on ubiquitous transmission Raman signal reception.

With reference to FIG. 1, a schematic representation of an exemplary embodiment transmission Raman analysis system and/or substance analysis system is indicated generally by the reference numeral 100. The system 100 is configured to analyze a substance 102 contained in a container 104 without removing the substance 102 from the container 104 or opening the container 104 using non-invasive stand-off analysis. The system 100 includes an energy source, such as a radiation source, shown in FIG. 1 as a laser 106. In multiple exemplary embodiments, the laser 106 is a diode laser. In one such embodiment, the laser 106 emits radiation with a wavelength of between approximately 10 nanometers (nm) and approximately 1.1 micrometers. In another embodiment, the laser 106 emits radiation with a wavelength of between approximately 785 nm and approximately 920 nm. In another embodiment, the laser 106 emits radiation with a wavelength of approximately 785 nm. In other embodiments, other suitable radiation sources may be used, for example fluorescence. In some embodiments described herein, Raman radiation, Raman signal, and/or Raman transmission can be substituted with other types of energy and/or radiation that can be emitted by the laser 106, 506, 606 and/or detected by detector(s) 110, 510, 610.

The laser 106 is configured to direct a beam of radiation 108 at the container 104. The system 100 also includes a detector or collection optics defining a substantially collimated detection path between the substance and the system. The detector is illustrated in FIG. 1 as an exemplary charge-coupled device (CCD) detector 110. In other embodiments, other suitable detectors and/or collection optics, such as, for example, single channel detectors, vacuum phototubes, photomultiplier tubes, semiconductor devices, photodiodes, avalanche photodiodes, array detectors, CCD image detectors, infrared array detectors, or the like may be used where configured to define a substantially collimated detection path between the substance and the system. The detector 110 is disposed to be directable toward the container 104, such that the container 104 may remain in situ. In one specific embodiment, the detector 110 includes only an aperture or a collection aperture (and not a focusing lens), where the aperture is configured to allow a reflected beam of radiation from the container 104 and/or substance pass to the detector 110. The aperture can be of different suitable sizes/diameters. In one implementation, a detector 110 can include an aperture with a diameter of about 10 mm. Other examples of aperture sizes can include about 5 mm, and about 20 mm. It is contemplated that other aperture sizes may be utilized.

Substances to be analyzed may be found in and/or on various types of containers, such as, for example, glass containers, plastic containers, plastic containers including high density polyethylene (HDPE) and/or polyethylene terephthalate (PET), paper containers, clear containers, generally transparent containers, translucent containers, generally opaque containers, tinted containers, or the like. It may be useful to analyze substances regardless of which of these types of containers contains the substance.

In prior art systems configured to detect Raman radiation, laser light is focused on a location on a container and a detector is focused on the same location on the container. The signal detected by a focused detector is collected back-scatter (e.g., collected from reflected energy, reflected generally around 180°, etc.) from the substance illumination zone. This back-scattered signal may tend to be indicative of the material of the container itself, especially if the container is generally opaque. That is, the Raman signal emitted might only be indicative of the surface layer, and in the case of a container containing a substance, might only be indicative of the material from which the container is formed, and might not be sufficiently indicative of the material of the substance contained in the container, such as in some containers with low transmission efficiency where low amounts of energy may pass through the container, low amounts of energy may be emitted from the container, and higher amounts of background energy from the container itself may be present.

With further reference to FIG. 1, in embodiments of the system 100, the beam of radiation 108 emitted by the laser 106 is configured such that a portion of the radiation from the laser 106 passes through a wall of the container 104 and into the substance, regardless of whether the container is generally transparent, translucent, or generally opaque.

Figure 2:
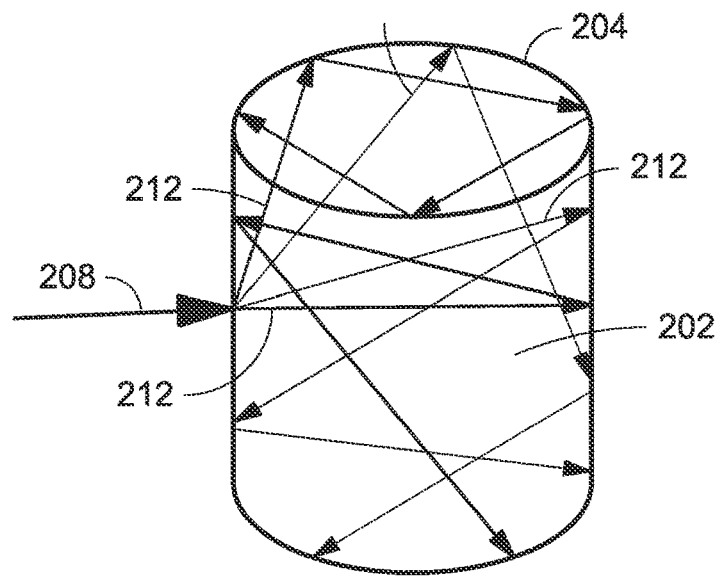
FIG. 2 is a schematic illustration of a beam of radiation impinging on a substance, illustrated here as within an opaque wrapper or container, but with the walls of the opaque wrapper or container shown transparently for illustrative purposes only, and illustrating exemplary paths of radiation within the opaque wrapper or container.

With reference to FIG. 2, a beam of radiation 208 directed at a generally opaque container 204 containing a substance 202 is illustrated. While in the illustrated embodiment the container 204 is generally opaque, the walls of the container 204 are shown transparently for illustrative purposes so that the movement of radiation 212 from the beam of radiation 208 that passes through the container 204 and into the substance may be easily seen. Generally, a portion of the beam of radiation 208 does not pass through and/or is reflected from the opaque container 204. Another portion of the radiation 212 passes through the container 204. For example, in one embodiment, approximately 1% of the radiation from the beam of radiation 208 passes through the generally opaque container. The portion of the radiation 212 that passes through the container 204 is scattered by the substance 202 and passes through the substance 202 in various directions. At least some of the radiation 212 is also reflected proximate the interface between the substance 202 and the container 204. Thus, having been reflected, the radiation 212 will again travel through the substance 202 by a path different than its original path, and then may again be reflected proximate the interface between the substance 202 and the container 204. Thus, portions of radiation make multiples passes with multiple different paths through different locations in the substance 202. The radiation 212 tends to encounter molecules of the substance in various different locations in the substance. Radiation 212 scatters throughout the substance, such as portions of the substance that do not absorb or block the radiation. The radiation 212 may be diffusely or randomly scattered.

Figure 3:
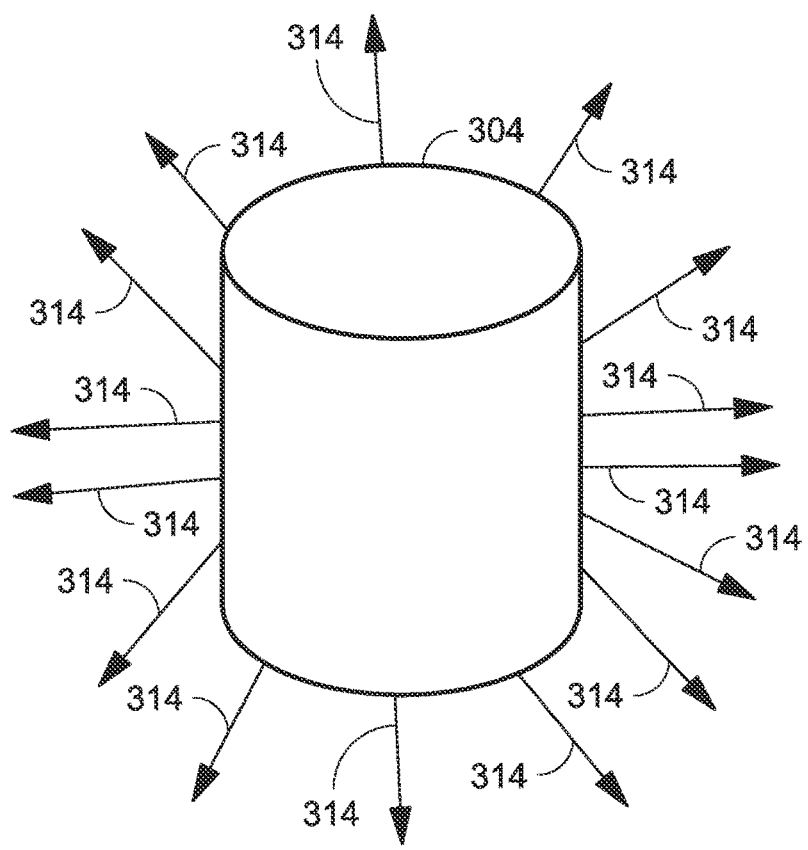
FIG. 3 is a schematic illustration of Raman radiation being emitted from the opaque wrapper or container of FIG. 2.

With reference to FIGS. 2 and 3, the molecules of the substance 202 in different locations encountering the radiation emit Raman radiation 314 in various different directions, at least a portion of which Raman radiation 314 passes through the container 304. A transmission Raman signal includes a combination of this Raman radiation from the various different molecules at different locations in the substance, e.g., a "bulk" signal, indicative of the components contained in the substance at various locations. In one embodiment, Raman analysis does not rely on absorption of the radiation 212, and a transmission Raman signal may be representative of the entire substance, such as not limited to the container material, coatings, outer portions of substances surrounding inner portions of substances, or the like.

With further reference to FIG. 1, in one embodiment, the detector 110 is configured to detect the transmission Raman signal, e.g., the "bulk" signal, combination of Raman signals emitted from different locations of and/or different molecules in the substance 102 from a variable stand-off distance while remaining in situ, etc. In some embodiments the detector 110 can be configured to detect other types of energy and/or radiation. For example, the system 100 and detector 110 can be configured to detect fluorescence. The transmission Raman signal is emitted in various directions from the opaque container 304 (see FIG. 3), and detection of the transmission Raman signal from the substance in the opaque container has a low angular dependency or low variation based on detection angle. In the embodiment illustrated in FIG. 1, the beam of radiation 108 is directed at a first location 116 on the container 104, while the detector 110 is directed at a second location 118. Unlike other systems, because the detector 110 does not require receiving back-scattered radiation from the beam of radiation 108, the first location 116 and the second location 118 need not be the same. In the illustrated embodiment, the first location 116 is an angular distance θ from the second location 118.

In one embodiment, the portion of the container through which the radiation passes is between approximately 0.004 inches and 0.12 inches in thickness. In one embodiment, the laser 106 has a power of between approximately 50 mW and approximately 500 mW. In embodiments of the system 100, the power of the laser 106 is sufficient and the detector 110 is sufficiently sensitive to detect a transmission Raman signal from a substance contained in a generally opaque container, such as a container where the portion of the container through which the radiation passes is between approximately 0.004 inches and 0.12 inches in thickness.

In one embodiment, when the container 104 is generally opaque, the transmission Raman signal is indicative of the substance itself and is not overwhelmed by the background signal from the container material 104. For example, the transmission Raman signal is indicative of the substance 102, and not appreciably obscured by a signal indicative of the type of material from which the container is formed regardless of the magnitude of non-zero angular distance θ between the first location 116 and the second location 118.

In one embodiment, the system 100 is further configured to analyze substances in generally transparent containers. When the beam of radiation 108 reaches the generally transparent container, a larger portion of the radiation of the beam passes through the container 104 and into the substance 102 than when the container is generally opaque. Here, the radiation in the substance 102 may tend to reflect within the substance 102 proximate the interface between the substance 102 and the container 104 generally less than when the container 104 is generally opaque, meaning that less of the substance 102 will encounter radiation from the beam of radiation 108. That is, the radiation may travel to fewer locations in the substance than, for example, in a generally opaque container in which the radiation may be reflected multiple times and pass throughout the substance. For example, the radiation may generally encounter the substance only generally along the path of the beam of radiation in containers without substantial internal reflection. However, Raman radiation is emitted by some molecules in the substance 102 encountering the radiation. The combination of Raman radiation from different locations in the substance provides a transmission Raman signal of the substance in the transparent container.

In one embodiment, when the container 104 containing the substance 102 is generally transparent, the intensity of the transmission Raman signal may be angularly dependent. In one embodiment, the detector 110 may sense the greatest intensity Raman signal from a substance 102 in a generally transparent container 104 when the angular distance θ between the first location 116 and the second location 118, e.g., angular distance between location on the container 104 to which the laser 106 is directed and the location on the container to which the detector 110 is directed, is approximately 135°. In one embodiment, the detector 110 may sense local maximum intensities of the Raman signal from a substance 102 in a generally transparent container when the angular distance θ between the first location 116 and the second location 118 is approximately 45° or when the angular distance θ between the first location 116 and the second location is approximately 90°.

In one embodiment, when the container 104 containing the substance 102 is generally transparent, when the angular distance θ between the first location 116 and the second location 118 is approximately 180°, the signal detected by the detector 110 is indicative of the material of the container, such as where the background signal of the bottle material is greater so the signal emitted by the substance is generally undetectable at the outer radiation entry point on the container 104.

With further reference to FIG. 1, in one embodiment, the system 100 also includes a processor 120. The processor 120 is coupled to the laser 106 and to the image detector 110. The processor 120 is configured to receive information regarding the transmission Raman signal from the detector 110 and to utilize this information to analyze the substance 102.

Figure 4:
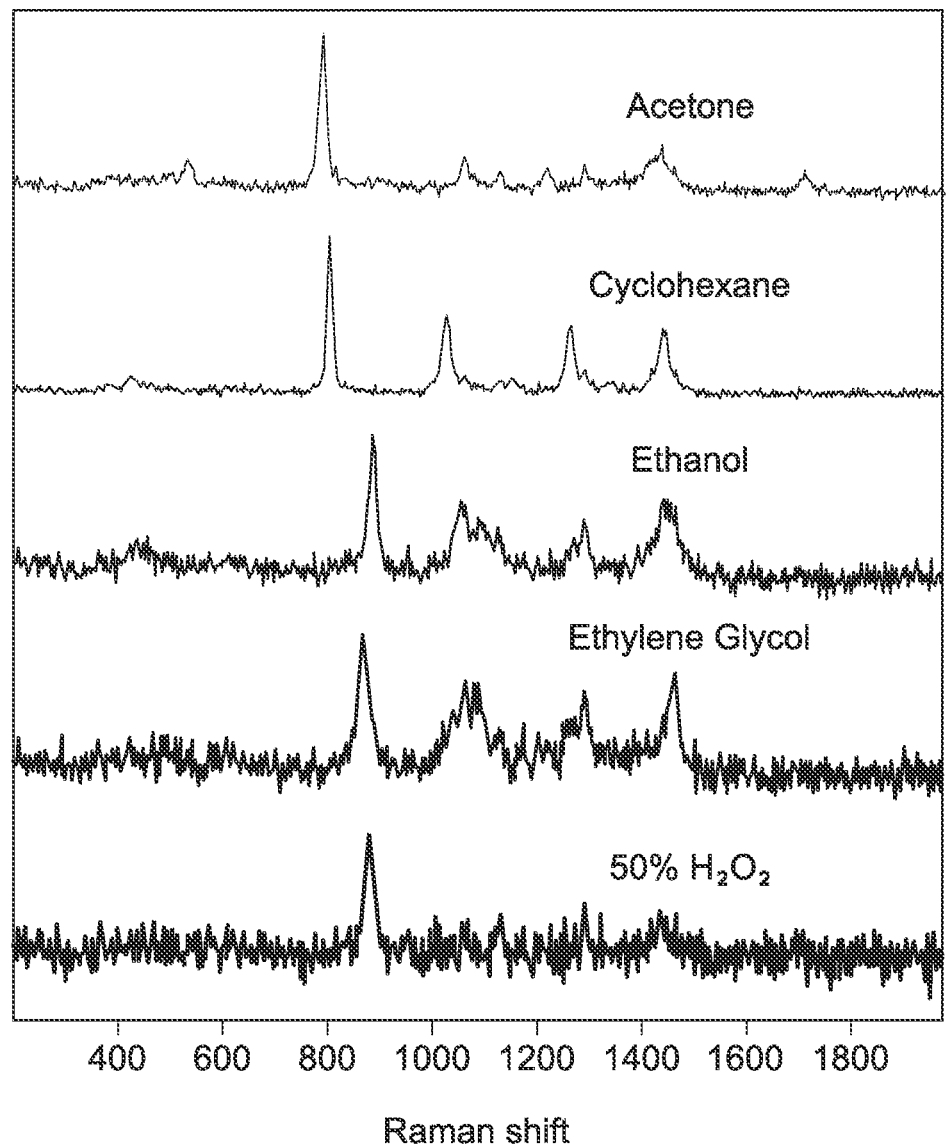
FIG. 4 is a graph showing Raman spectra indicative of exemplary substances of interest contained in generally opaque wrappers or containers, plotted on axes of Raman shift vs. Raman intensity.

With reference to FIGS. 1 and 4, in one embodiment, the processor 120 includes a comparator module configured to compare characteristics of the transmission Raman signal, e.g., wavelength, etc., with characteristics of the beam of radiation 108 to analyze the substance 102. FIG. 4 illustrates a graph showing the Raman spectra of various exemplary components that may be of interest contained in a generally opaque container. For example, the energy difference between the transmission Raman signal and the beam of radiation 108 may be compared to determine the Raman spectrum, e.g., fingerprint, of the substance. In the embodiment illustrated in FIG. 4, the x-axis is the Raman shift, in the illustrated embodiment in units of wavenumber. In one embodiment, this may be determined by subtracting the wavelength of the beam of radiation 108 from the wavelength of the transmission Raman signal. In one embodiment, the y-axis is the intensity. In one embodiment, the intensity may be determined from the detector 110 based on the transmission Raman signal received.

In one embodiment, the processor 120 includes a library of signal characteristics indicative of components in substances that may be of interest (e.g., dangerous components, illicit components, impurities, etc.). The processor 120 is configured to compare the characteristics of the transmission Raman signal received by the detector 110 with information in the library of signal characteristics to determine whether a substance contains components of interest. In one embodiment, the processor 120 is configured to output to a user an indication of whether or not a substance contains one of the predetermined components with characteristics stored in the library, e.g., visual output, audio output, electric signal output, etc.

With further reference to FIG. 1, in one embodiment, the system 100 includes an additional sensor 122. This additional sensor 122 is configured to indicate when a container 104 is located relative to the system 100 such that a substance 102 contained in the container 104 may be analyzed by the system 100. In one embodiment, the additional sensor 122 is coupled to the laser 106. In another embodiment, the additional sensor 122 is coupled to the processor 120. In one embodiment, the sensor 122 is pressure sensor configured to output a signal when a container 104 is properly located relative to the system 100. In another embodiment, the sensor 122 is an optical sensor configured to detect when a container 104 is properly located relative to the system 100. In other embodiments, other suitable sensors may be used.

In one embodiment, existing analysis devices, such as, e.g., a ResponeR BLS™, commercially available from Smiths Detection®, etc., may be retrofit to perform embodiments of methods described above.

In one embodiment, the container 104 is formed from plastic. In another embodiment, the container 104 is formed from glass. The laser 106 is configured to emit a beam of radiation such that sufficient radiation passes through the container 104 and into the substance 102 so that the substance 102 will emit a transmission Raman signal sufficient to be detected by the detector 110. In one embodiment, the laser 106 has a power of between approximately 50 milliwatts (mW) and approximately 500 mW. In one embodiment, the sidewall of the container 104 is between approximately 0.1 mm and approximately 3 mm thick. In one embodiment, substances contained in containers formed from HDPE may be analyzed by embodiments of systems 100 described above.

In various embodiments, systems 100 described above configured to analyze substances in containers may provide the ability to analyze substances in opaque containers without removing the substances from the containers. In some embodiments, the system 100 may be configured to minimize the background signal from the material of the container itself to allow analysis of the substance within the container. In some embodiments, relative insensitivity to optical alignment of the radiation source and the detector may allow for high throughput (e.g., large volume of substances analyzed in short period of time, etc.), reliable detection of components of interest within substances, and a low rate of false alarm (e.g., low number of occurrences of indication from processor of component of interest being present in a substance when in fact no component of interest is present in the substance, low number of occurrences of indication from processor of component of interest not being present in substance when in fact component of interest is present in the substance, etc.).

In other embodiment, multiple energy sources located at multiple locations and directing light at multiple locations on a container containing a substance may be provided. In one embodiment, this configuration with multiple energy sources may improve signal collection efficiency.

In another exemplary embodiment implementation using ubiquitous transmission Raman spectroscopy, such as with the transmission Raman substance analysis system 100, a radiation beam from laser 106, which may emit focused or non-focused probe light, is directed through the wall or bottom of container 104. The laser beam becomes a diffusive light source within the container 104 with no formation of a distinct substance region. In this implementation, a whole liquid substance 102 is illuminated by the internal reflection of lasers between the inner walls of the container 104. A Raman signal is generated from multi-path laser excitation of the whole liquid substance 102 within the container 104. The ubiquitous Raman signal can be transmitted and received in omni-direction. Advantages of using transmission Raman spectroscopy can include a transparent, sufficiently transparent, and/or opaque delivery region (e.g., bottle material or the like). Additionally, the substance region can include the whole liquid substance 102. The collection optics (e.g., detector 110) can include focus and/or non-focus optics, and the laser light beam within the substance 102 can function as a diffusive light source. The whole liquid substance 102 can be illuminated due to the internal reflection of the laser beams. The Raman signal source can be from multi-path laser excitation instead of only from a single laser beam path. Using non-focus optics can prevent burning on dark-colored materials (e.g., plastic bottles, labels, or the like). Further, the Raman signal collection can be from the whole container 104 because of the omnidirectional collection, and the delivery region and the collection path can be non-concentric as well as concentric.

Figure 5:
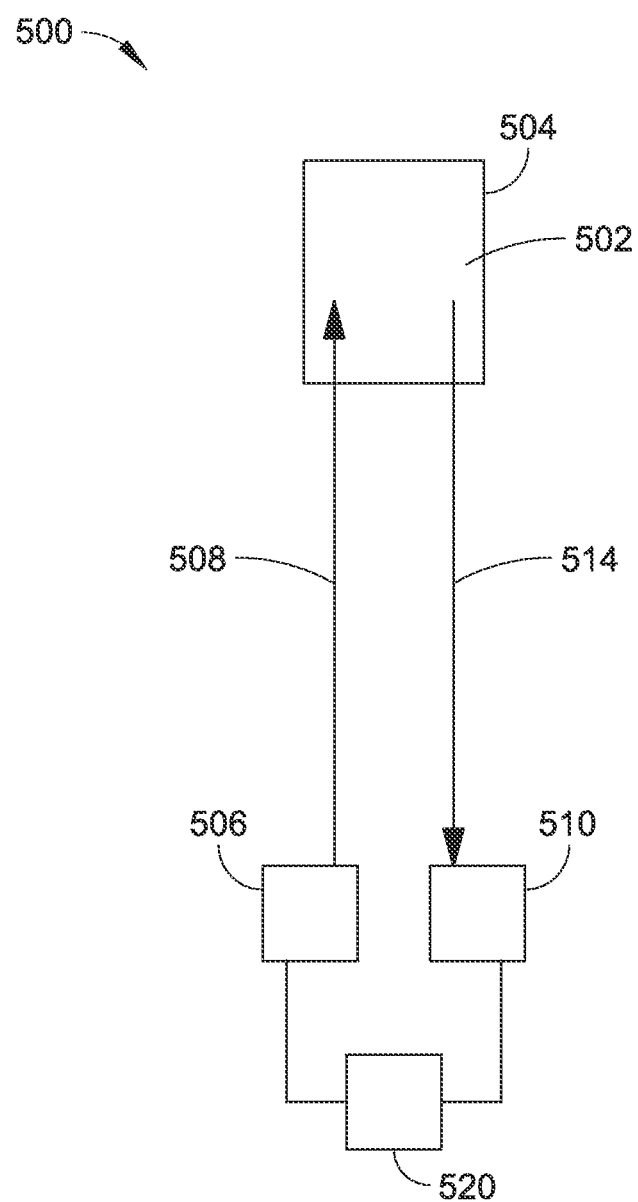
FIG. 5 is a schematic illustration of an exemplary system embodiment configured to remotely analyze a substance from a stand-off distance, without moving or contacting the substance, based on a ubiquitous transmission Raman signal reception, where the transmitter and receiver are fixed relative to each other.

With reference to FIG. 5, a schematic representation of an exemplary embodiment transmission Raman substance analysis system is indicated generally by the reference numeral 500. The system 500 is configured to analyze a remote substance 502 contained in and/or on a container 504 without removing the substance 502 from the container 504 or opening the container 504. The system 500 includes an energy source, such as a radiation source (e.g., Raman-type, fluorescence), shown in FIG. 5 as a laser 506. In multiple exemplary embodiments, the laser 506 can be a diode laser. In one such embodiment, the laser 506 emits radiation with a wavelength of between approximately 10 nanometers (nm) and approximately 1.1 micrometers. In another embodiment, the laser 506 emits radiation with a wavelength of between approximately 785 nm and approximately 920 nm. In another embodiment, the laser 506 emits radiation with a wavelength of approximately 785 nm. In other embodiments, other suitable radiation sources and wavelengths may be used, such as Raman scattering and/or fluorescence. Further, the laser 506 can be configured to provide focused or non-focused energy and/or radiation.

The laser 106 is configured to direct a beam of radiation 508 at the container 504, which can be remote (e.g., a variable stand-off distance from the substance while in situ) from the laser 506 and/or detector 510. In the context of the system 500, remote can mean that the substance is not necessarily touching the laser 506 and/or detector 510 and may not be located within system 500 (e.g., the remote substance 502 can be 6 inches from the laser 506 and/or detector 510, the remote substance 502 can be 3 feet from the laser 506 and/or the detector 510, etc.). In some implementations, remote can include a variable stand-off distance while remaining in situ. The system 500 also includes a detector 510, illustrated in FIG. 5, for example a charge-coupled device (CCD) detector 510. In other embodiments, other suitable detectors 510, such as, for example, single channel detectors, vacuum phototubes, photomultiplier tubes, semiconductor devices, photodiodes, avalanche photodiodes, array detectors, CCD image detectors, infrared array detectors, or the like may be used. The detector 510 can be configured to be directed toward the container 504 and receive reflected radiation 514 from the container 504 through an aperture and/or a collective aperture. In one specific embodiment, the detector 510 includes a collective aperture with a diameter of about ten (10) mm. In the embodiment shown in FIG. 5, the beam of radiation 508 and the reflected radiation 514 can be substantially co-axial, although in some other embodiments, the beam of radiation 508 and the reflected radiation 514 are not necessarily co-axial. In the embodiment, shown in FIG. 5, the laser 506 can emit radiation such that the radiation (e.g., laser beam) is collimated or substantially collimated from the laser 506 to the detector 510 along the collection path, including after traveling through and/or on a remote substance 502 and/or container 504. For example, the radiation emitted from the laser 506 can be directed to a remote substance 502 and the radiation can be reflected along the same or similar path in a collimated fashion to the detector 510. In this embodiment, the radiation 508 emitted from the laser 506 and radiation 514 reflected from the substance 502 and/or container 504 travels along a 360-degree angular distance between the laser 506 and the detector 510. In some implementations, the collimated light can have an approximate diameter of ten (10) mm, although the detector 510 can detect and/or collect other collimated light dimensions.

Figure 6:
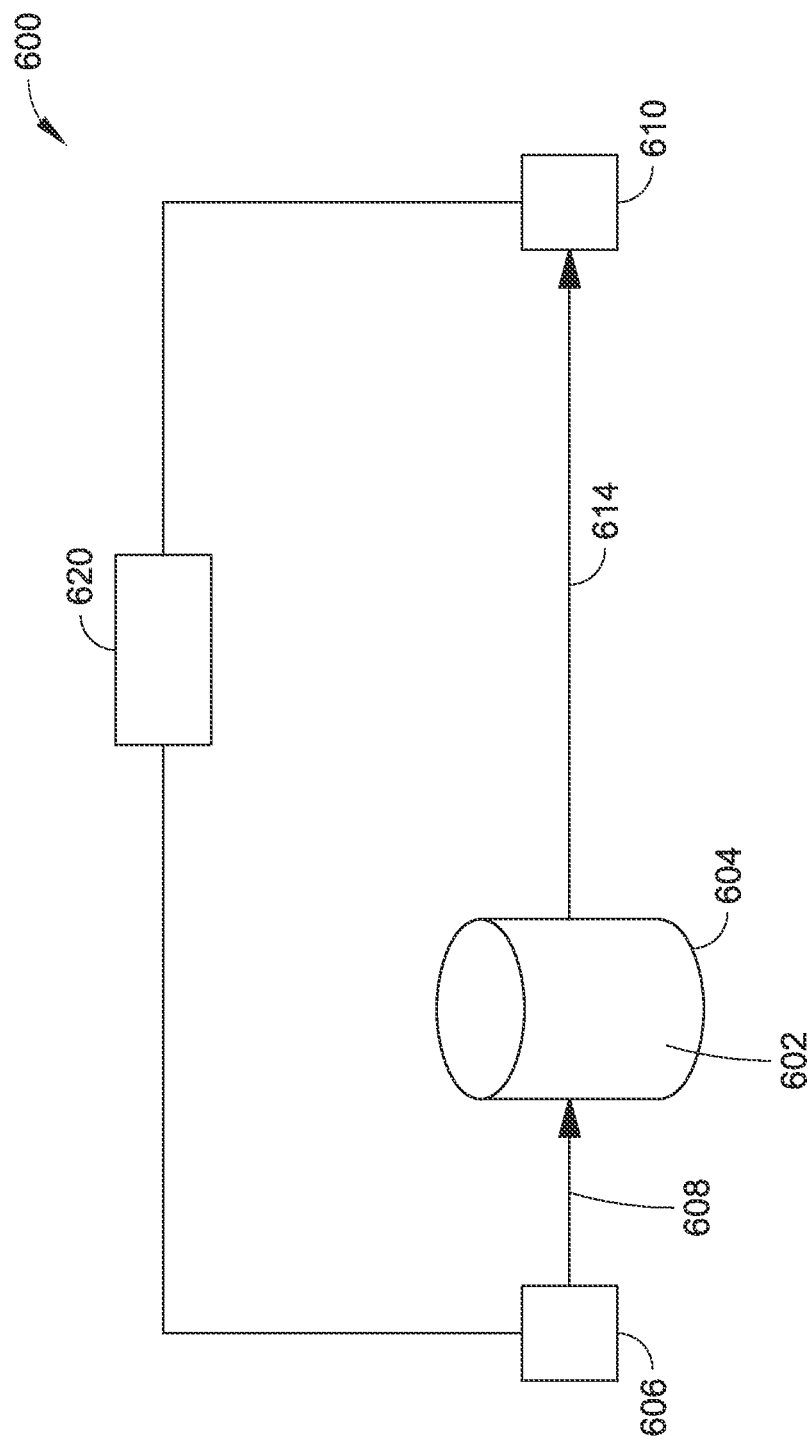
FIG. 6 is a schematic illustration of an exemplary system embodiment configured to remotely analyze a substance from a stand-off distance, without moving or contacting the substance, based on a transmission Raman signal reception, where the transmitter and receiver are movable relative to each other.

With reference to FIG. 6, a schematic representation of an exemplary embodiment transmission Raman substance analysis system is indicated generally by the reference numeral 600. The system 600 is configured to analyze a remote (e.g., a variable stand-off distance from the substance while in situ) substance 602 contained in and/or on a container 604 without removing the substance 602 from the container 604 or opening the container 604. The system 600 includes an energy source, such as a radiation source, shown in FIG. 6 as a laser 606. In multiple exemplary embodiments, the laser 606 can be a diode laser. In one such embodiment, the laser 606 emits radiation with a wavelength of between approximately 10 nanometers (nm) and approximately 1.1 micrometers. In another embodiment, the laser 606 emits radiation with a wavelength of between approximately 785 nm and approximately 920 nm. In another embodiment, the laser 606 emits radiation with a wavelength of approximately 785 nm. In other embodiments, other suitable radiation sources may be used. Further, the laser 606 can be configured to provide focused or non-focused energy and/or radiation.

In FIG. 6, the laser 606 is configured to direct a beam of radiation 608 at the container 604, which can be remote from the detector 610. In the context of the system 600, remote can mean that the substance is not necessarily touching the laser 606 and/or detector 610 and may not be located within system 600 (e.g., the remote substance 602 can be 6 inches from the laser 606 and/or detector 610, the remote substance 602 can be 3 feet from the laser 606 and/or the detector 610, etc.). FIG. 6 illustrates the laser 606 directing a beam of radiation 608 to and through a container 604 and substance 602, where reflected radiation 614 from the substance 602 is detected by detector 610, which is remote from the substance 602 in this embodiment. The system 600 as illustrated in FIG. 6, can include a detector 610 that is a charge-coupled device (CCD) detector 610. In other embodiments, other suitable detectors 610, such as, for example, single channel detectors, vacuum phototubes, photomultiplier tubes, semiconductor devices, photodiodes, avalanche photodiodes, array detectors, CCD image detectors, infrared array detectors, or the like may be used. The detector 610 can be configured to be directed toward the container 604 and receive reflected radiation 614 from the container 604. In the embodiment shown in FIG. 6, the beam of radiation 608 and the reflected radiation 614 can be substantially co-axial and/or collimated. In this embodiment, the radiation 614 emitted from the laser 606 travels along a generally zero-degree angular distance between the laser 606 and the detector 610. In other embodiments, the bean of radiation 608 and the reflected radiation 614 are not substantially co-axial.

In one embodiment, a system 100 may be configured to analyze containers containing multiple substances, e.g., multi-container.

In one embodiment, a system 100 may be configured to determine the composition of a container and to determine the composition of a substance in the container, e.g., another detector may be directed at a location on a container, e.g., approximately 180° from a location on a container to which an energy source is directed, etc., and configured to detect a signal from the container material itself.

In an exemplary embodiment, no reference beam is used, and container or bottle background is recognized and removed if substantial. In this exemplary embodiment, a single collection path may be used to collect the Raman signal. If the container background component is found to be relatively strong, other means to remove it are used, such as a characteristic lookup table for particular materials. The characteristic lookup table may include predicted Raman signals for various types of glass and/or plastic.

Additionally, one method for transmission Raman analysis can include emitting radiation with a radiation source and/or laser towards a first wall portion of a container, wherein the emitted radiation becomes a diffusive light source within the container without formation of a distinct substance region; and receiving, with a detector, a transmission Raman signal through a second wall portion of the container, the received signal including Raman radiation reflected from multiple portions of the container. A similar method can be utilized to detect other types of reflected radiation, energy, light, and/or signals, for example fluorescence.

Another method for analyzing a substance in a container having an interior surface and an exterior surface can include directing a beam of radiation at the container such that at least a portion of the radiation passes through the container and is scattered in the substance and at least a portion of the scattered radiation reflects off of the interior surface of the container, the radiation in the substance resulting in emission of a Raman signal representative of the contents of the substance at a plurality of locations within the substance; detecting the Raman signal representative of the contents of the substance at a plurality of locations within the substance; and comparing the Raman signal to the radiation of the radiation source. A similar method can be utilized to detect other types of reflected radiation, energy, light, and/or signals, for example fluorescence.

Another method for analyzing a liquid substance in both generally opaque to visible light containers and generally transparent containers, respectively, includes directing a beam of radiation at a first location on a container containing a liquid substance; directing a detector at a second location on the container, the second location being different from the first location; wherein the beam of radiation and the detector are configured so a sufficient amount of radiation from the beam passes through the container and into the substance to produce a sufficient transmission Raman signal including Raman radiation from a plurality of locations in the substance so the detector can detect the transmission Raman signal, the transmission Raman signal being indicative of the composition of the substance; comparing the transmission Raman signal with the radiation emitted by the emitter; determining based on a library of characteristics of components of interest whether the transmission Raman signal indicates that the substance contains a component of interest; and outputting whether or not the substance contains a component of interest.

Embodiments of processors 120 may include analog-to-digital converters, digital-to-analog converters, amplification elements, microprocessors, etc., as will be further explained below. Processors are not limited by the materials from which they are formed or the processing mechanisms employed therein. For example, the processor may be comprised of semiconductor(s) and/or transistors (e.g., electronic integrated circuits (ICs)). Memory can be included with the processor. Memory can store data, such as algorithms configured to compare. Although a single memory device can be used, a wide variety of types and combinations of memory (e.g., tangible memory) may be employed, such as random access memory (RAM), hard disk memory, removable medium memory, external memory, and other types of computer-readable storage media.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

In additional embodiments, a variety of analytical devices may make use of the structures, techniques, approaches, and so on described herein. A variety of analytical instruments may make use of the described techniques, approaches, structures, and so on. These devices may be configured with limited functionality (e.g., thin devices) or with robust functionality (e.g., thick devices). Thus, a device's functionality may relate to the device's software or hardware resources, e.g., processing power, memory (e.g., data storage capability), analytical ability, and so on.

In embodiments, the system, including its components, operates under computer control. For example, a processor included with or in the system to control components and functions described herein using software, firmware, hardware (e.g., fixed logic circuitry), manual processing, or a combination thereof. The terms "controller" "functionality," "service," and "logic" as used herein generally represent software, firmware, hardware, or a combination of software, firmware, or hardware in conjunction with controlling the system. In the case of a software implementation, the module, functionality, or logic represents program code that performs specified tasks when executed on a processor (e.g., CPU or CPUs). The program code may be stored in one or more computer-readable memory devices (e.g., memory and/or one or more tangible media), and so on. The structures, functions, approaches, and techniques described in this document can be implemented on a variety of computing platforms having a variety of processors.

Memory can be included with the processor. The memory can store data, such as a program of instructions for operating the system (including its components), data, and so on. Although a single memory device can be used, a wide variety of types and combinations of memory (e.g., tangible memory, non-transitory) may be employed, such as random access memory (RAM), hard disk memory, removable medium memory, external memory, and other types of computer-readable storage media.

Although this disclosure has described embodiments in a structural manner, the structure and its structural and/or functional equivalents can perform methods.

Variations of the embodiments disclosed in this document will be apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although the invention has been described in language specific to structural features and/or methodological acts, it is to be understood that the invention defined in the appended claims is not necessarily limited to the specific features or acts described. Rather, the specific features and acts are disclosed as example forms of implementing the claimed invention.

What is claimed is:

1. A substance analysis system disposable a variable stand-off distance from a substance in situ, the system comprising:
    an emitter disposed to emit radiation onto a first region of the substance in a container in situ; and
    a detector disposed the variable stand-off distance from the substance in situ, the detector comprising a receiver defining a substantially collimated collection path over the variable stand-off distance, where the collection path is unfocused on any distinct substance region within the container so that the detector receives radiation from a second region of the substance, wherein the second region is larger than the first region and the angular distance between the first region and the second region is equal to or greater than 90 degrees and less than 180 degrees,
    wherein the received radiation is representative of the entire substance, and
    wherein:
        the emitter emits radiation into the first region of the substance in the container along an emission direction,
        the detector receives radiation from the second region of the substance along a radiation collection direction, and
        the angular distance between the first region and the second region is defined as an angle between the emission direction and the radiation collection direction.

2. The system of claim 1 wherein the receiver is configured to receive a transmission Raman signal from a substantially columnar portion of the substance.

3. The system of claim 1, wherein the system is configured to analyze substances within at least one of a container that is substantially opaque to visible light and a container substantially transparent to visible light.

4. The system of claim 1, further comprising a sensor configured to determine when a container is configured relative to the system such that a substance within the container may be analyzed by the system.

5. The system of claim 1, further comprising a processor configured to indicate the presence of predetermined components within the substance based on the output of a comparator.

6. The system of claim 1, further comprising a comparator configured to compare the wavelength of the received Raman signal with the wavelength of the emitted radiation.

7. A method of transmission Raman analysis comprising:
    emitting radiation towards a first wall portion of a container in situ onto a first region of a sample in the container, wherein emitted radiation becomes a diffusive light source within the sample in the container without formation of a distinct substance region; and
    receiving a transmission Raman signal through a second wall portion of the container, the received signal including Raman radiation reflected from multiple portions of the sample within the container, the received signal including Raman radiation collected from a second region of the sample in the container, wherein the second region is larger than the first region and the angular distance between the first region and the second region is equal to or greater than 90 degrees and less than 180 degrees,
    wherein the receiver is disposable a stand-off distance from the container in situ, and
    wherein the Raman signal is received through a collection path that is substantially collimated and unfocused on any distinct substance region within the container, the Raman signal being representative of the sample, and
    wherein:
        emitting radiation onto the first region of the sample in the container comprises emitting radiation onto the first region along an emitter initial transmission axis,
        receiving the Raman radiation collected from the second region of the sample in the container comprises collecting the Raman radiation along the detector collection axis, and the angular distance between the first region and the second region being defined as an angle between the emitter initial transmission axis and the detector collection axis.

8. The method of claim 7, further comprising comparing the transmission Raman signal with the emitted radiation.

9. The method of claim 7, wherein no reference beam is used, the method further comprising:
receiving a Raman signal including container background information;
looking up matching container background information; and
subtracting the looked-up container background information from the received Raman signal.

10. The method of claim 9, wherein the matching container background information is selected from a table comprising entries for a plurality of glass types and a plurality of plastic types.

11. The method of claim 7, wherein at least one of the emitted radiation or Raman radiation illuminates the entire contents of the container by the internal reflection of radiation between the inner walls of the container.

12. The method of claim 7, wherein a Raman signal is generated from multi-path excitation of a whole liquid substance within the container.

13. The method of claim 7, wherein the Raman signal is at least one of omni-directional or ubiquitous.

14. The method of claim 7, wherein the container is generally opaque to visible light.

15. The method of claim 7, wherein said first wall portion is defined by an outer surface of the container, and said second wall portion is defined by an inner surface of the container directly interior to said outer surface.

16. A method of analyzing a substance in a container in situ a variable stand-off distance from a substance analysis system, the container having an interior surface and an exterior surface, the method comprising:
directing a beam of radiation at the container onto a first region of a sample in the container such that at least a portion of the radiation passes through the container and is scattered in the substance and at least a portion of the scattered radiation reflects off of the interior surface of the container, the radiation in the substance resulting in emission of a Raman signal representative of the entire substance;
detecting the Raman signal representative of the entire substance, wherein the emitted Raman signal is collected from a second region of the sample in the container, wherein the second region is larger than the first region and the angular distance between the first region and the second region is equal to or greater than 90 degrees and less than 180 degrees, and the Raman signal is detected through a collection path that is substantially collimated and unfocused on any distinct substance region within the container; and
comparing the Raman signal to the radiation of the radiation source, and
wherein:
directing the beam of radiation onto the first region of a sample in the container comprises emitting the beam of radiation along an emission path having a first direction,
collecting the emitted Raman signal from the second region of the sample in the container comprises collecting the emitted Raman signal along the collection path having a second direction and the angular distance between the first region and the second region is defined as an angle between the emission path having the first direction and the collection path having the second direction.

17. The method of claim 16, further comprising:
wherein the directing comprises at least one of:
directing a beam of radiation at a container generally opaque to visible light and detecting the Raman signal representative of the contents of a substance contained in the generally opaque container; or
directing a beam of radiation at a non-opaque container and detecting the Raman signal representative of the contents of a substance contained in the non-opaque container.

18. The method of claim 16, wherein the substance comprises a liquid substance.

19. The method of claim 16, wherein the radiation source is configured to emit a beam of radiation such that a substance contained in a generally opaque container will emit a transmission Raman signal for detecting the Raman signal.

20. The method of claim 16, wherein the radiation in the substance is reflected in the container; and
wherein the radiation travels in the substance resulting in emission of Raman radiation at various angular orientations with respect to each other, respectively.

21. A method of analyzing liquid substances in both generally opaque to visible light containers and generally transparent containers, respectively, using a substance analysis system disposable a variable stand-off distance from the liquid substances in situ, comprising:
directing a beam of radiation at a first location on a container containing a liquid substance, wherein the beam of radiation is directed into a first region of the liquid substance in the container;
directing a detector at a second location on the container, the second location being different from the first location;
wherein the beam of radiation and the detector are configured so that radiation from the beam passes through the container and into the substance to produce a transmission Raman signal including Raman radiation from a plurality of locations in the substance so the detector can detect the transmission Raman signal, wherein the transmission Raman signal is collected from a second region of the liquid substance in the container, wherein the second region is larger than the first region and the angular distance between the first region and the second region is equal to or greater than 90 degrees and less than 180 degrees, and wherein the transmission Raman signal is received through a collection path that is substantially collimated and unfocused on any distinct substance region within the container, the transmission Raman signal being indicative of the entire composition of the substance;
comparing the transmission Raman signal with the radiation emitted by the emitter;
determining based on a library of characteristics of components of interest whether the transmission Raman signal indicates that the substance contains a component of interest; and
outputting whether or not the substance contains a component of interest, and
wherein:

directing the beam of radiation into the first region of the liquid substance in the container comprises directing the beam of radiation along an emission path direction, collecting the transmission Raman signal from the second region of the liquid substance in the container comprises collecting the transmission Raman signal along the collection path direction, and the angular distance between the first region and the second region is defined as an angle between the emission path direction and the collection path direction.

22. The method of claim 21, wherein detection of the transmission Raman signal from the substance in the container is angularly independent of the beam of radiation when the beam of radiation is directed at a generally opaque container that is opaque to visible wavelengths of light.

23. The method of claim 21, further comprising determining whether the transmission Raman signal indicates that the substance contains at least one of acetone, cyclohexane, ethanol, ethylene glycol, or $H_2O_2$ and outputting a warning if it is determined that the transmission Raman signal indicates that the substance contains at least one of acetone, cyclohexane, ethanol, ethylene glycol, or $H_2O_2$.

24. The method of claim 21, wherein the first location is approximately 135° from the second location.

25. A substance analysis system disposable a variable stand-off distance from a container in situ, the system comprising:

an emitter configured to emit radiation directed at a first location on the container, at least a portion of the radiation passing through the container and into a substance in the container onto a first region of the substance in the container, with at least a portion of the radiation in the substance being reflected within the container; and a detector with a receiving portion directed at a second location on the container, the detector being configured to receive a transmission Raman signal including Raman radiation from multiple portions of the substance, wherein the transmission Raman signal is collected from a second region of the sample in the container, wherein the second region is larger than the first region and the angular distance between the first region and the second region is equal to or greater than 90 degrees and less than 180 degrees, the Raman signal being representative of the entire substance, wherein the Raman signal is received through a collection path that is substantially collimated and unfocused on any distinct substance region within the container, wherein the radiation directed at a first location on the container and the Raman radiation are substantially co-axial, and wherein:

an emission path is defined as extending between the emitter and the first region of the substance in the container and along an emitter initial transmission axis, the collection path is defined as extending between the second region and the detector and along a detector collection axis, and the angular distance between the first region and the second region is defined as an angle between the emitter initial transmission axis and the detector collection axis.

26. The system of claim 25, wherein the emitter is configured to emit focused radiation.

27. The system of claim 25, wherein the emitter is configured to emit non-focused radiation.

28. The system of claim 25, wherein the emitter is a stationary laser.

29. A substance analysis system disposable a variable stand-off distance from a container in situ, the system comprising:

a detector with a receiving portion directed at the container, the detector being configured to receive a reflected radiation signal from multiple portions of a substance in the container, wherein the reflected radiation signal is based on a beam of radiation signal directed onto a first region of a sample within the container, the detector a stand-off distance from the container, where the receiving portion of the detector includes a collection aperture configured to receive a substantially collimated beam of radiation reflected from the substance in the container, wherein the beam of radiation is unfocused on any distinct substance region within the container, and wherein the reflected radiation signal is representative of the entire substance, and wherein the reflected radiation signal is collected from a second region of the sample in the container, the second region being larger than the first region and the angular distance between the first region and the second region is equal to or greater than 90 degrees and less than 180 degrees and wherein:

the beam of radiation directed onto the first region of a sample within the container comprises emitting the beam of radiation along an emission path having a first direction, collecting the reflected radiation signal from the second region of the sample in the container comprises collecting the reflected radiation signal along a collection path having a second direction and the angular distance between the first region and the second region is defined as an angle between the emission path having the first direction and the collection path having the second direction.

30. The substance analysis system of claim 29, where the collection aperture is approximately five mm in diameter.

31. The substance analysis system of claim 29, where the container is substantially opaque to visible wavelengths.

* * * * *